United States Patent [19]

White, Jr. et al.

[11] Patent Number: 5,647,371
[45] Date of Patent: Jul. 15, 1997

[54] SKIN TESTING DEVICE LOADING METHOD

[75] Inventors: William White, Jr.; Robert E. Esch, both of Lenoir; John A. Richardson, Charlotte, all of N.C.

[73] Assignee: Greer Laboratories, Inc., Lenoir, N.C.

[21] Appl. No.: 421,617

[22] Filed: Apr. 12, 1995

[51] Int. Cl.⁶ .................................................. A61B 5/00
[52] U.S. Cl. .................................................. 128/743
[58] Field of Search .................. 128/743; 604/47, 604/191, 201; 206/367

[56] References Cited

U.S. PATENT DOCUMENTS

| | | | |
|---|---|---|---|
| D. 247,822 | 5/1978 | Hein et al. | D24/31 |
| 2,522,309 | 9/1950 | Simon . | |
| 3,289,670 | 12/1966 | Krug et al. . | |
| 3,556,080 | 1/1971 | Hein . | |
| 4,270,548 | 6/1981 | Brennan | 128/743 |
| 4,292,979 | 10/1981 | Inglefield et al. | 128/743 |
| 4,453,926 | 6/1984 | Galy | 604/47 |
| 5,027,826 | 7/1991 | Fishman | 128/743 |

*Primary Examiner*—Max Hindenburg
*Attorney, Agent, or Firm*—Bell, Seltzer, Park & Gibson, P.A.

[57] ABSTRACT

There is provided a method for performing skin tests for biologic response which includes providing an applicator having at least one pick having at least one skin piercing epidermal point and being capable of carrying a load of testing substance such as biologic substances, such as an antigen, for skin testing for each pick, each of said sources being carried in a container having an opening. The applicator is placed in sealing relationship over each of the openings in the container to form a single unit of the combined applicator and source. The unit is then inverted so as to load each pick with an effective amount of substance to perform a skin test, reverting said unit, and the applicator is removed in loaded condition ready for use. The testing substances are epicutaneously deposited by piercing the patient's skin with each pick to a predetermined depth and observing the pierced skin for response to the testing substance.

9 Claims, 1 Drawing Sheet

SKIN TESTING DEVICE LOADING METHOD

BACKGROUND OF THE INVENTION

1. Field of the Invention

The present invention relates to a method for performing skin tests for allergic or other diagnostic reason. More particularly, the present invention relates to a method for loading a skin test device used for epicutaneous application of biological or test substances.

2. The Prior Art

Diagnosis of allergies has relied upon a number of techniques for introducing various biological substances to the epidermis or dermis. In a widely accepted testing method for allergies and other immunologic conditions—the skin test— various biologicals, such as aeroallergens, food allergens, and other substances are applied by abrading, cutting or puncturing the epidermal skin layer and contacting the liquid allergenic extract or the like with the exposed skin tissue. The test areas are often on the back or arm of the patient and the tests normally cause some discomfort. If the patient is allergic to a particular biological substance which is applied, histamine or a histamine substance will be released by the affected tissue resulting in redness and swelling in that area. The specific test sites are then compared to a control test site to visually determine if the patient is allergic to a particular test substance.

The skin tests may be performed one test at a time with each allergenic extract being loaded onto a scarifier or pick and applied to the skin. An example of a device for applying single tests is shown in U.S. Pat. No. 4,270,548. As it is desirable to speed up the testing process, devices for performing multiple tests simultaneously were developed. One such multiple skin test device which is widely used is the applicator disclosed in U.S. Pat. No. 3,556,080 to Hein which discloses a plastic applicator having an elongated handle from which extend curved connecting legs, each one of which terminates in a pressure puncture head having a cluster of sharp points. The method of using the Hein multi-headed applicator is to place the applicator upside down with the rigid handle being supported in a holder, such as described in Hein's U.S. Design Pat. No. 247,822. Each of the pressure puncture heads or picks is then individually loaded with a testing substance by the doctor or the nurse. Once the puncture heads are individually loaded, the applicator is grasped by the elongated handle and then applied to the skin in a manner that each puncture head can penetrate the surface of the skin. Using this method, loading each puncture head individually, takes a considerable amount of time.

An early form of a multi-headed skin test applicator is disclosed in U.S. Pat. No. 2,522,309 to Simon which discloses what is alleged to be the first simultaneous inoculation testing device. In the Simon patent the applicator comprises test covers (handles) having attached needles which are placed over a plurality of allergen containing wells in a manner to allow the needles to enter the fluid. The covers fit snugly over the wells in a sealing relationship. When the multi-headed applicator is removed from the wells with a spiral motion, the needles touch the sides of the wells to remove excess allogenic extract. The thus loaded multi-headed applicator is then used in the normal manner.

The desire to simplify and speed-up allergy testing procedures has led to the development of a number of other multi-headed skin test applicators. The patent to Galy, U.S. Pat. No. 4,453,926 provides a multi-headed scarifying device for simultaneously performing a plurality of skin tests. The device has a clustered group of points that are contained in a hermetically sealed envelope with the envelope containing an active liquid substance into which the cluster points are immersed. To operate the Galy device one must individually remove each envelope tab.

U.S. Pat. No. 3,289,670 to Krug, et al. describes a multi-headed device for simultaneously performing a plurality of scratches on a patent to apply biological testing substances. The device has a multi-well structure with a flat upper surface and a plurality of wells in the upper surface of the structure. The device also includes a reusable abrading unit having a skin abrading member with multiple cluster points which fit on top of the structure so the members fit into each well and are immersed in the liquid testing substance. When the tests are performed the multi-headed abrading unit is removed from the well and applied to the patient in the normal manner.

The present invention overcomes the disadvantages of the prior art by providing a method for rapidly loading a skin testing applicator with biologicals or other test substances.

SUMMARY OF THE INVENTION

It has been found that the method of the present invention enables the user to rapidly and efficiently load a skin testing applicator used for epicutaneous application of biologicals or other test substances. The apparatus used to perform the method of the present invention includes an applicator having at least one pick having at least one skin piercing point and being capable of carrying a load of biological or other testing substance. Preferably, the applicator has a number of picks. The spacing between the applicator picks is such that the applicator may be placed over the openings of a container having a plurality of biological or other testing substances. The biological or other testing substances are placed in wells located in the upper surface of the container which are spaced according to the spacing of picks in the applicator. Thus, the applicator is adapted to fit tightly over each of the container openings.

The method of the invention is to hold the applicator over the container openings in a sealing relationship to form a single unit. The unit is inverted upside down to load each pick with an amount of testing substance effective to perform a scratch test. The effect of turning the unit upside down and reinverting the unit to its original position will load each of the picks in one motion as opposed to applying the testing substances individually to each pick. The loaded applicator is then used to pierce the patient's skin to a predetermined depth and the pierced skin is observed for response to the testing substance.

It is therefore an object of the present invention to provide a method for loading a pick used in performing a skin test with a testing substance.

Another object of the present invention is to provide a method for simultaneously performing a plurality of skin tests to determine the allergic response to the application of biological testing substances to the scratched skin.

Yet another object of the present invention is to provide a method for rapidly loading a multi-headed pick used for performing skin tests with biological testing substances.

BRIEF DESCRIPTION OF THE DRAWINGS

Other objects, features and advantages of the invention will be apparent from the detailed description of the invention when taken in conjunction with the accompanying drawing, in which.

DESCRIPTION OF THE PREFERRED EMBODIMENTS

Figures 1, 2, 3, 4:
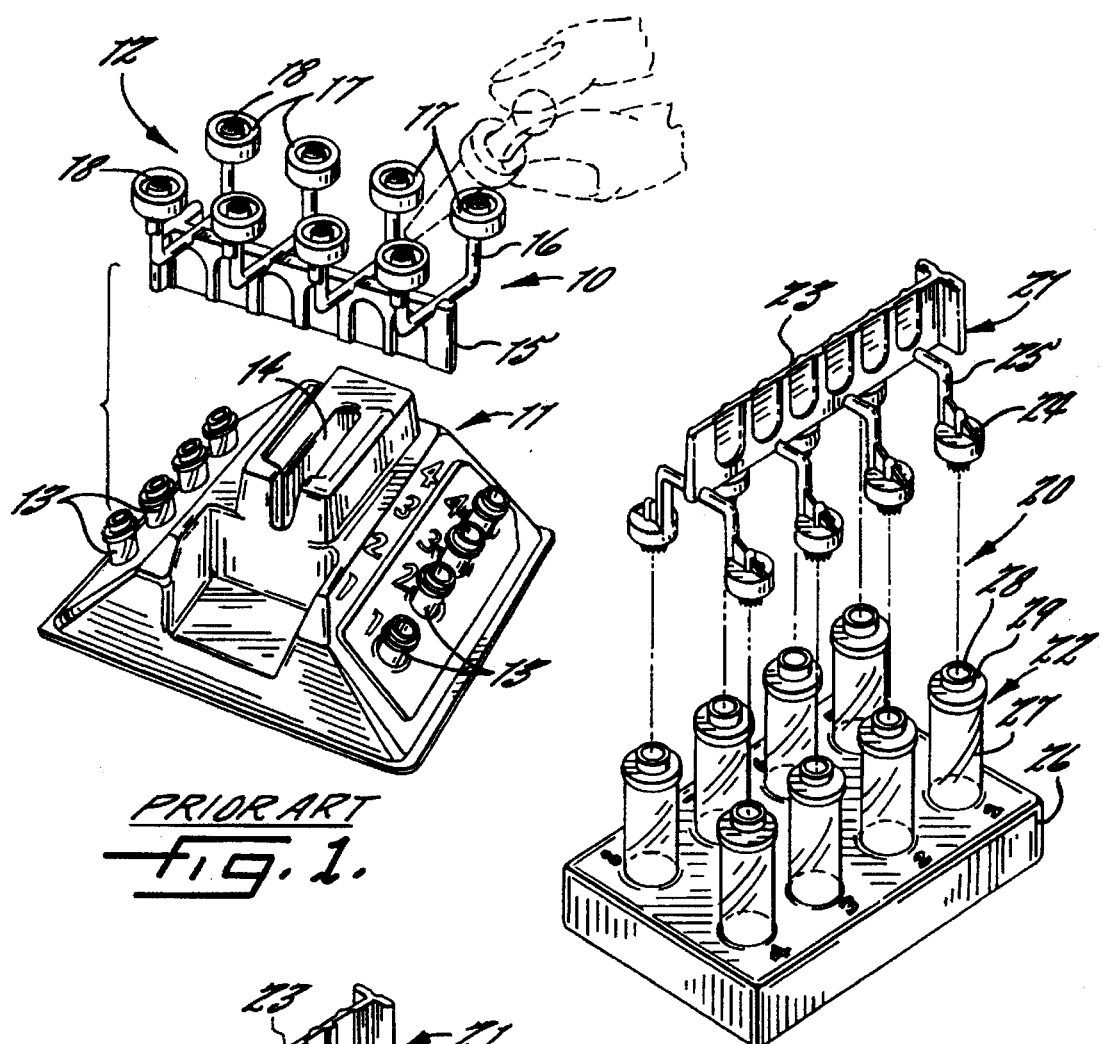
FIG. 1 is a perspective view of a multi-headed applicator for conducting simultaneous skin tests being loaded according to a method of the prior art.
FIG. 2 is an exploded perspective view showing separately a multiple headed skin test applicator and a container providing a source for a plurality of test substances for use in the method of the present invention.
FIG. 3 is an environmental view illustrating initiation of the method of the present invention.
FIG. 4 is an environmental view illustrating the single unit used in the method of the present invention in inverted position.

There is shown in FIG. 1 one of the presently popular methods of the prior art for carrying out simultaneous skin tests. Use of the device shown in FIG. 1 requires individually loading each pick. This prior art device is shown generally at 10 and comprises a base 11 and a multiple head applicator 12. The base 11 includes eight wells numbers 1 through 8 adapted to hold a number of vials 13 of biological or other testing substances and an applicator retainer member 14 adapted to hold applicator 12 while each pick or pressure puncture head 17 of the applicator 12 is being individually loaded with the testing substance. A suitable base member has been described, for example, in Hein, et al., U.S. Design Pat. No. 247,822. The applicator 12 has a relatively rigid elongated handle 15 from which extend connecting legs 16, each one of which terminates in a pressure puncture head 17 having a cluster of points 18. After the applicator 12 has been loaded with testing substance it is applied epicutaneously to the patient's skin by scratching or piercing the skin to a predetermined depth. One such applicator used for this purpose is described in U.S. Pat. No. 3,556,080.

Turning now to the present invention, there is shown in FIG. 2 a skin test device, designated generally as 20, which may be used in the method of the present invention. The skin test device 20 includes a multi-headed applicator 21 and a source 22 of biological or other testing substances for skin testing. The applicator preferably has the same number of picks as there are sources of testing materials. It should be understood that the applicator used in the method of the present invention may have a single puncture pick and the source may be a single source.

In the embodiment shown in FIG. 2, the multi-headed applicator 21 has an elongated body 23 forming a relatively rigid handle. The handle may be of a variety of styles and shapes so long as it may be easily grasped in one hand. The multi-headed applicator 21 also includes a plurality of individual pressure puncture heads or picks 24, forming a scarifier portion having at least one skin piercing epidermal point and being capable of carrying a load of testing substance. The elongated handle 23 and the individual picks 24 are connected by legs 25. The picks 24 are placed along the elongated handle 23 in such position that when the multi-headed applicator 21 is placed over the opening to the source of testing substances, a liquid tight seal is obtained. In a preferred embodiment, each vial has a sealing member 29 which fits snugly into the opening 28 and which is adapted to form a liquid tight seal when the applicator is placed into the opening. The picks are suitably spaced apart from each other to reduce the risk of overlapping readings. The handle portion and the scarifier portion of the applicator may be separate members that are connected when used. It should be understood that a variety of embodiments of the applicator may be used in the method of this invention so long as the sealing relationship is obtained during loading.

The source 22 of biological or other testing substances for skin testing includes a series of wells or, as shown, a series of vial holders, located in stand member 26. As stated, the stand or holder 26 has a plurality of openings for holding vials 27 in an upright position, each having an opening 28. The number of wells or openings in each stand, and their geometric arrangement, can be adapted for several types of test devices. Ordinarily about 8 to 12 wells are placed in a unit to provide maximum ability to perform the method of this invention. The well sites are preferably marked to easily keep track of each testing substance. The stand or vial holder 26 is of such size and shape as to permit the user's hand to fit over the rigid handle 23, when the handle is in sealed relationship with the vial opening 28, and grasp the sides of stand member 26 as shown in FIG. 3.

Among the preferred biological or other testing substances are allergens selected from the group consisting of tree allergens, mold allergens, grass allergens, ragweed allergens, dust, epidermals and weed allergens.

The method for skin testing includes placing antigens into groups of closely related components for simplicity. Typically, inhalant or aeroallergens are divided into seven or eight groups depending on the antigens found in a particular geographical location. Food antigens may also be divided into groupings.

These antigens are then applied by the to the test sites on the patient's arm or back along with control test substances of the particular diluent used and one of histamine. The purpose of using a control is to insure against false-positive reactions.

The preferred groupings of inhalant antigens include extracts of pollens, molds, dust, epidermals, insects and foods. The antigen may be used in either an aqueous form or a glycerin-saline base. For trees, weeds, and grasses, the preferred concentration is 50 grams/liter (g/l). For mold, epidermals and house dust, the preferred concentration is 100 g/l.

Method of the Invention

In accordance with the present invention there is shown in FIGS. 3, the positioning of the user's hand when initiating the method for performing skin tests for allergic response of this invention. The method provides an applicator having a plurality of individual picks, each of the picks comprising a scarifier portion having at least one skin piercing epidermal point and being capable of carrying a load of testing substance. There is also provided a source of biological or other testing substances for skin testing for each pick, each of the testing sources being carried in a container having an opening. The applicator is placed in sealing relationship over each of the openings to form a single unit of the combined applicator and source. As shown in FIG. 4, the entire unit is inverted so as to load each pick with an effective amount of testing substance to perform a skin test. The unit is reinverted so that the unit is up right and the applicator is removed in loaded condition. The applicator is then used to deposit the testing substances epicutaneously by piercing the skin with each pick to a predetermined depth. The pierced skin is observed for response to the testing substance.

The present invention has been described in detail with particular reference to preferred embodiments and the operation thereof, but it is understood that variations, modifications, and the substitution of equivalent means can be effected within the spirit of this invention.

What is claimed is:

1. A method for performing skin tests for biologic response which comprises the steps of:

providing an applicator having at least one pick, said pick having at least one skin piercing epidermal point and being capable of carrying a load of testing substance;

providing a source of test substances for each pick, each of said sources being carried in a container having an opening for each source and arranged in said container so as to accommodate each pick of said applicator;

placing said applicator in sealing relationship over each of said openings to form a single unit of the combined applicator and source;

inverting said single unit so as to load each pick with an effective amount of said testing substance to perform a skin test; and reinverting said unit to its upright position, and removing said applicator in loaded condition ready for performing skin tests.

2. The method for performing skin tests for biologic response according to claim 1 further comprising depositing said testing substance epicutaneously by piercing the patient's skin with each pick to a predetermined depth; and observing the pierced skin for response to said testing substance.

3. The method for performing skin tests for biologic response according to claim 1 wherein said testing substance is an antigen.

4. The method for performing skin tests for biologic response according to claim 1 wherein each of said picks comprises is loaded with a predetermined effective amount of allergens selected from the group consisting of tree allergens, mold allergens, grass allergens, ragweed allergens, dust, epidermals and weed allergens.

5. The method for performing skin tests for biologic response according to claim 1 wherein said antigen is provided in a concentration of about 50 to 100 grams per liter.

6. The method for performing skin tests for biologic response according to claim 1 wherein said testing source comprises a mixture of aeroallergens.

7. The method for performing skin tests for biologic response according to claim 1 wherein said applicator has a plurality of picks.

8. A method for allergy testing for multiple allergen screening comprising:

providing an applicator having a plurality of individual picks, each of said picks having at least one skin piercing epidermal point and being capable of carrying a load of testing substance;

providing a source of antigens for skin testing for each pick, each of said antigens being carried in a container having an opening;

placing said applicator in sealing relationship over each of said openings to form a single unit of the combined applicator and source;

inverting said single unit so as to load each pick with an effective amount of antigen to perform a skin test;

reverting said unit and removing said applicator in loaded condition;

depositing said antigen epicutaneously by piercing the patient's skin with each pick to a predetermined depth; and observing the pierced skin for response to said antigen.

9. The method for performing skin tests for biologic response according to claim 8 wherein each of said picks comprises and is loaded with a predetermined effective amount of admixed allergens selected from the group consisting of tree allergens, mold allergens, grass allergens, ragweed allergens, dust, epidermals and weed allergens.

* * * * *

UNITED STATES PATENT AND TRADEMARK OFFICE
CERTIFICATE OF CORRECTION

PATENT NO. : 5,647,371
DATED : July 15, 1997
INVENTOR(S) : White, Jr. et al.

It is certified that error appears in the above-identified patent and that said Letters Patent is hereby corrected as shown below:

On the title page, column 1, U.S. Patent Documents, line 6, "Inglefield et al" should be --Inglefield, Jr. et al --.

Column 1, line 62, "allogenic" should be -- allergenic --.

Column 2, line 9, "patent" should be --patient--.

Column 4, line 29, omit "by the".

Column 4, line 58, "up right" should be --upright--.

Claim 5, line 30 (Claim 4) delete "comprises".

Column 6, line 32 (Claim 9) delete "comprises and".

Signed and Sealed this

Nineteenth Day of May, 1998

Attest:

BRUCE LEHMAN

*Attesting Officer*  *Commissioner of Patents and Trademarks*